United States Patent [19]
Teves

[11] Patent Number: 5,957,902
[45] Date of Patent: Sep. 28, 1999

[54] SURGICAL TOOL FOR ENLARGING PUNCTURE OPENING MADE BY TROCAR

[76] Inventor: Leonides Y. Teves, 1607 54th St. W., Bradenton, Fla. 34209

[21] Appl. No.: 09/161,791

[22] Filed: Sep. 28, 1998

[51] Int. Cl.$^6$ .............................. A61M 5/00; A61B 17/34; A61B 1/22
[52] U.S. Cl. ........................... 604/264; 606/185; 600/201
[58] Field of Search .................................... 606/185, 108, 606/190, 191, 198; 604/264; 600/201, 204, 206, 219

[56] References Cited

U.S. PATENT DOCUMENTS

| | | | |
|---|---|---|---|
| 5,176,659 | 1/1993 | Mancini | 604/280 |
| 5,320,611 | 6/1994 | Bonutti et al. | 604/264 |
| 5,814,073 | 9/1998 | Bonutti | 606/232 |

*Primary Examiner*—Glenn K. Dawson
*Assistant Examiner*—Jennifer Maynard
*Attorney, Agent, or Firm*—Smith & Hopen, P.A.; Ronald E. Smith

[57] ABSTRACT

A surgical tool of the type used with a trocar expands the diameter of a puncture opening made in a body cavity so that a linear incision is not needed in certain surgical procedures. An elongate base member of cylindrical construction is divided into a plurality of parts by cuts that extend the longitudinal extent of the base member in circumferentially spaced relation to one another and the parts are bound together and held into a solid cylindrical configuration by a plurality of longitudinally spaced apart bias members such as rubber bands. A plunger has an elongate leading end that drives the base member parts in a radially outward direction, increasing the diameter of the puncture opening, when it is inserted into the base member. The bias members restore the parts of the base member to their position of repose when the leading end of the plunger is withdrawn from the base member. The trailing end of the base member is received within a transversely disposed housing that helps hold the assembly together as the parts of the base member are expanded or retracted. To use the tool, a trocar punctures the cavity and carries part of the leading end of the base member into the cavity. The trocar is withdrawn, leaving the base member in place, and the leading end of the plunger is then inserted into the base member to expand it. Surgical tools are sequentially inserted through the bore of the leading end of the plunger. The diameter of that bore is sufficient to enable removal of an enlarged gall bladder or the like from the cavity.

10 Claims, 4 Drawing Sheets

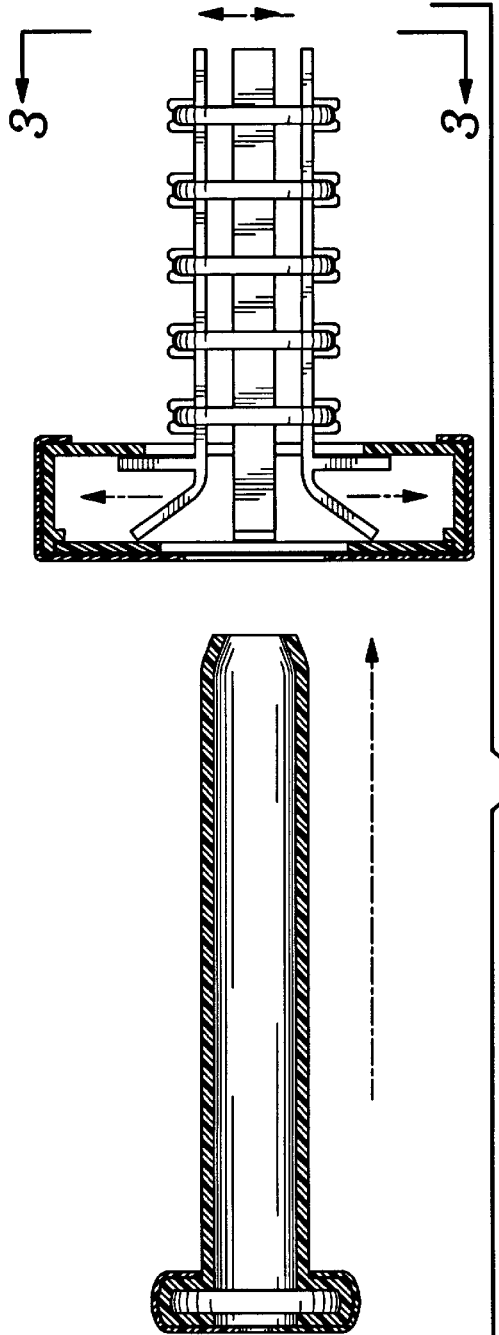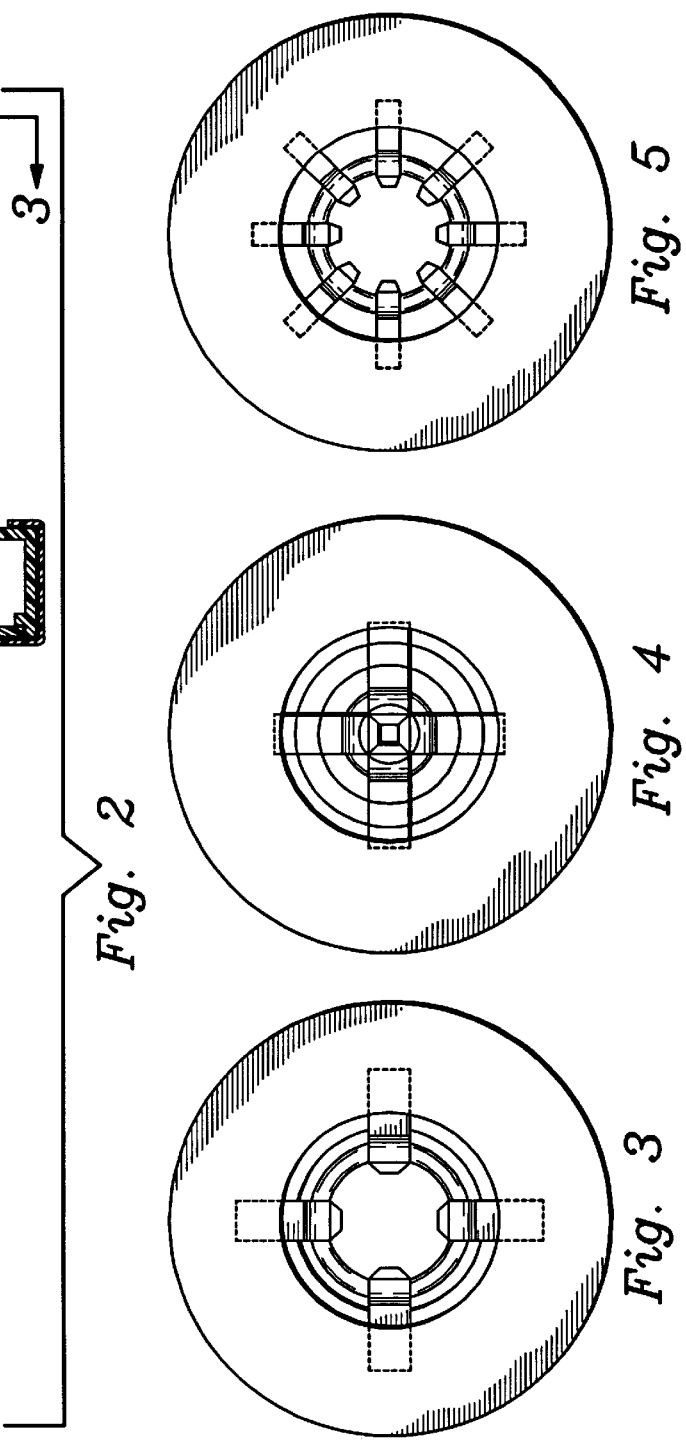

SURGICAL TOOL FOR ENLARGING PUNCTURE OPENING MADE BY TROCAR

BACKGROUND OF THE INVENTION

1. Field of the invention

This invention relates, generally, to surgical tools. More particularly, it relates to a surgical tool that expands an opening initially formed in a body cavity by a trocar.

2. Description of the Prior Art

Surgery often begins with the making of an elongate incision. As is well known, healing of such incisions requires a lengthy recovery time. A trocar is therefore sometimes used in those situations where an incision can be avoided.

A trocar is a sharp-pointed surgical tool used to pierce a body cavity, such as the abdominal cavity, for example. More particularly, a trocar is a straight metallic rod having a pointed leading end that forms a puncture opening of substantially round shape. A surgeon can then perform surgical procedures through the puncture opening, thereby avoiding a conventional incision and reducing the post-operative recovery time for the patient.

The puncture opening is held open by a cannula that is carried by the trailing end of the trocar and which remains in place when the trocar is withdrawn; the cannula may serve as a drainage outlet. It may also serve as a passageway for the insertion of surgical tools such as used in arthroscopy and laparoscopy.

Since the advent of miniature cameras and fiber optics, the cannula may also be used as a passageway for insertion into the body cavity of a camera and lighting means so that a physician may view the interior of the cavity.

For example, it is possible to remove a gall bladder by using a conventional trocar, but only if the diseased gall bladder is small enough to be retracted from the body cavity through the cannula. If the gall bladder is too large to be pulled through the passageway defined by the cannula, then the initial puncture opening must be enlarged by means of a conventional incision.

What is needed, then, is an improved trocar that is not subject to the limitations of conventional trocars.

However, in view of the art considered as a whole at the time the present invention was made, it was not obvious to those of ordinary skill in this art how the art could be advanced.

SUMMARY OF THE INVENTION

The long-standing but heretofore unfulfilled need for an apparatus that overcomes the limitations of the prior art is now met by a new, useful, and nonobvious invention. The present invention is a tool used with a trocar that includes an elongate base member having a leading end and a trailing end. The base member is of cylindrical construction but it is formed of separate parts that are radially expandable with respect to a longitudinal axis of the base member.

A rod-shaped trocar having a length greater than the length of the base member is slideably inserted into the trailing end of the base member so that the pointed leading end of the trocar extends beyond the leading end of the base member; said pointed leading end is used in the conventional way to puncture a preselected body cavity.

Significantly, the base member has a length sufficient to enable the base member to serve the same function as a cannula in prior art trocar tools. Thus, after the puncture opening has been made, the trocar is retracted from the base member and the base member is left in place, i.e., the trailing end of the base member is left outside the body cavity and the leading end thereof is left inside the body cavity. Accordingly, surgical tools may be inserted through the hollow passageway of the base member just as if it were a cannula. The lengthening of the base member relative to the base members of the prior art thus serves to eliminate the need for a cannula.

A transversely disposed housing receives the trailing end of the base member. The housing has a predetermined diameter greater than a predetermined diameter of the elongate base member so that the housing limits the distance to which the base member may be inserted into the body cavity. The housing also serves as a handle means for the physician. Moreover, it provides expansion space and a means for guiding the respective parts of the base member when the base member is expanded.

The base member is formed of a plurality of separate parts that are formed by cutting a cylindrical tube with a plurality of longitudinally-extending, circumferentially-spaced apart cuts.

A plurality of flexible and resilient, stretchable bias means are disposed about the base means at predetermined, longitudinally-spaced intervals, to hold together the separate parts of the base member when it is in repose. The base member has a solid cylindrical configuration when in repose. When not in repose, i.e., when expanded, the individual parts of the base member are circumferentially spaced apart from one another but the expansion means drives each part of the base member a common distance in a radially outward direction with respect to a longitudinal axis of symmetry of the base member.

The expansion means is a hollow plunger having an elongate, cylindrical leading end that is inserted into the trailing end of the base member to cause the expansion of the base member. The base member housing has an opening to accommodate the plunger.

The hollow plunger has a transversely disposed handle means at its trailing end; the handle means of the plunger, like that of the base member, has a greater diameter than the elongate cylindrical leading end thereof to limit travel of the leading end into the base member and to serve as a handle means for the physician.

The housing of the base member and the handle means of the plunger both include a seal means at their respective trailing ends. The seal means at the trailing end of the base member housing seals around the periphery of the leading end of the plunger when it is inserted into the base member, and the seal at the trailing end of the plunger handle seals about the periphery of a surgical tool that is inserted therethrough. The cylindrical leading end of the plunger has a predetermined external diameter greater than the predetermined internal diameter of the base member so that sliding insertion of the leading end of the plunger into the base member causes the separate parts of the base member to expand radially outwardly with respect to a longitudinal axis of symmetry of the base member.

The cylindrical leading end of the plunger also has a predetermined internal diameter that is greater than the internal diameter of the base member when the base member is in repose.

When the parts of the base member are in their expanded configuration, having been driven into said configuration by the leading end of the plunger, surgical tools are then inserted through the plunger to perform the operation. An enlarged gall bladder, for example, may be removed through the bore of the plunger whereas such an enlarged gall bladder may have been too large to remove through a conventional cannula.

By selecting a plunger from an assortment of plungers having leading ends of differing diameters, a physician can determine the amount of radial expansion of the initial puncture opening. In many cases, an expanded puncture opening will obviate the need for a conventional incision.

It is a primary object of this invention to provide a trocar tool that can be used to remove enlarged gall bladders or other diseased or malfunctioning body parts.

A more specific object is to provide a trocar tool having means for expanding an initial puncture opening in a way that does not require the making of a conventional incision.

A closely related object is to provide a trocar too that minimizes the discomfort of and the post-operative recovery time required for a patient.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 2 is a bracketed view depicting the novel plunger in longitudinal section and the novel expandable base member in the same partially sectional side elevation as FIG. 1;

FIG. 3 is an end view taken along line 3—3 in FIG. 2;

FIG. 4 is an end view like FIG. 3, but depicting the parts of the expandable base member when in repose, i.e., when in their unexpanded configuration;

FIG. 5 is an end view like FIG. 3, depicting a second embodiment of the expandable base in its expanded configuration;

DETAILED DESCRIPTION OF THE PREFERRED EMBODIMENT

Figure 1:
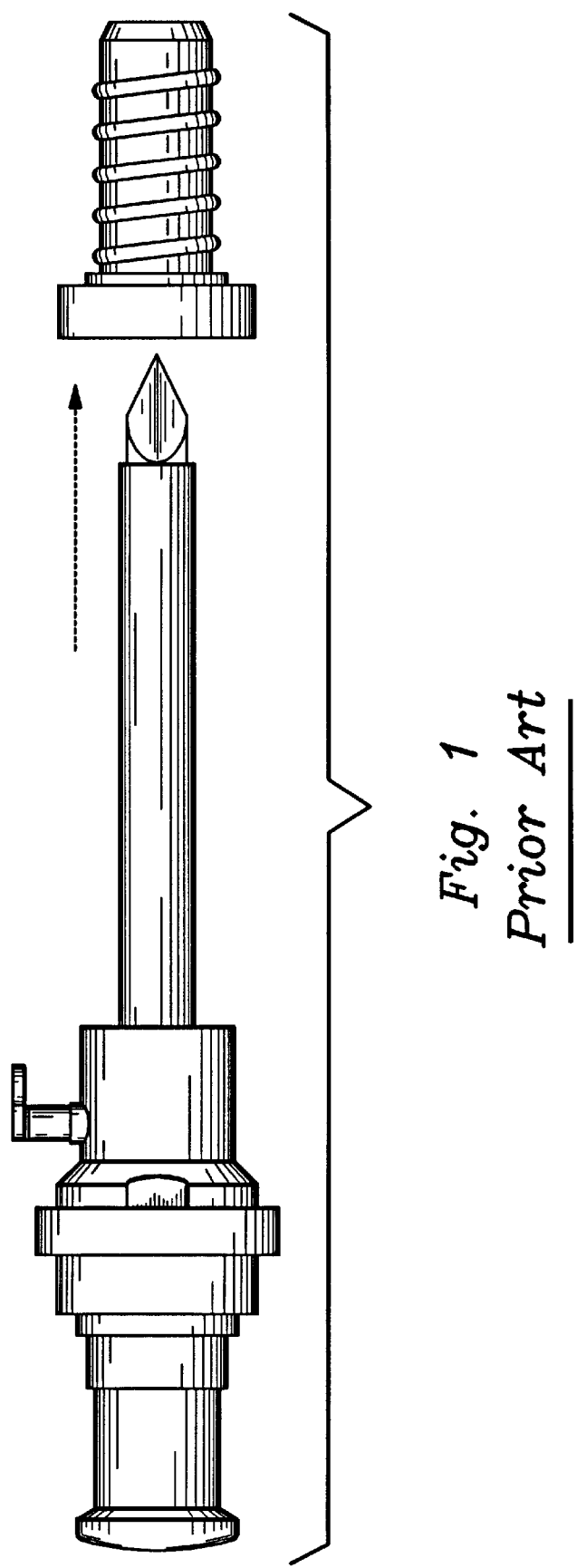
FIG. 1 is a bracketed view depicting the novel plunger in side elevation and the novel expandable base member in a partially sectional side elevation.

Referring now to FIG. 1, it will there be seen that an exemplary embodiment of the invention is denoted as a whole by the reference numeral 10. The primary parts of the novel assembly include hollow plunger 12, expandable base member 14, housing 16, and a plurality of bias members, collectively denoted 18.

Novel tool 10 eliminates the need for a cannula as in the prior art because base member 14 is elongated relative to the cannula holders of the prior art.

Figure 6:
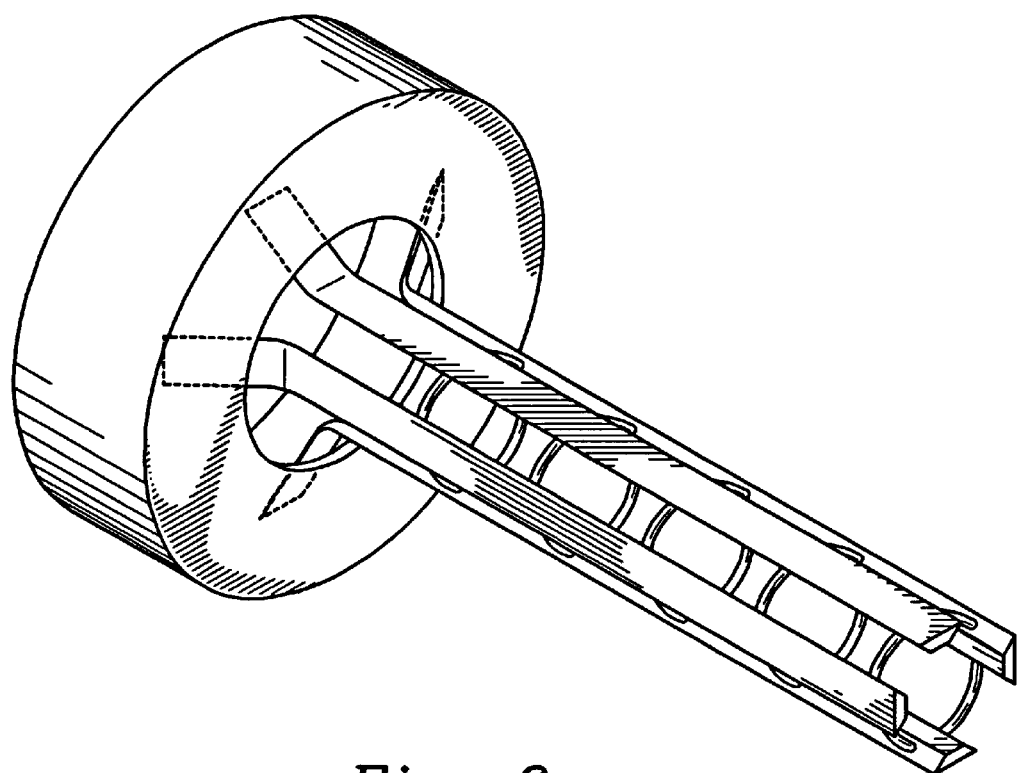
FIG. 6 is a perspective view of the expandable base member depicted in FIGS. 1–4.

In this particular embodiment, and as perhaps best understood in connection with FIGS. 3 and 6, base member 14 is divided into four equal-sized parts denoted 14a, 14b, 14c and 14d, but it should be understood that it could be made in as few as two parts, theoretically, or it could be made of five or more parts, and still perform the same work, function in substantially the same way, and achieve the same results.

The parts are made by cutting a hollow, cylindrical base member 14 into plural parts, preferably but not necessarily of the same size. The cuts extend longitudinally and are parallel to one another and are circumferentially spaced relative to one another. Thus each part 14a, 14b, 14c and 14d of base member 14 has the same longitudinal extent as the other parts and, preferably, the same circumferential extent.

Base member 14 is not cylindrical for its entire extent; its trailing end 15(a–d) is flared radially outwardly at a predetermined angle as depicted.

Bias members 18 may be provided in the form of rubber bands or similar elastomeric bands, bungee cords, coil springs, or the like. They are wrapped about the collective peripheries of the base member parts and serve to hold said parts together as depicted in FIG. 4 when the bias members are in repose. The number of bias members is not critical, but each of them is preferably disposed transversely to a longitudinal axis of symmetry of base member 14.

As best understood in connection with FIGS. 1 and 2, hollow plunger 12 has a transversely disposed handle 11 at its trailing end and an elongate, cylindrical leading end 13 having an external diameter greater than the internal diameter of base member 14 when said base member is in repose, i.e., when said base member is in its contracted configuration. Thus, as leading end 13 of plunger 12 is slidingly introduced into the trailing end 15(a–d) of base member 14, it causes a radially outward expansion of base member parts 14a, 14b, 14c and 14d, said expansion being resisted but not prevented by said bias members 18. Such expansion increases the diameter of the puncture made by the trocar, and eliminates, in most cases, any need to enhance the size of the initial puncture opening by making a conventional incision.

Leading end 13 of plunger 12 defines a bore 13a (FIG. 2) having an internal diameter greater than the internal diameter of base member 14 when said base member is in repose. Preferably, the internal diameter of bore 13a is also greater than or at least equal to the internal diameter of base member 14 when said base member is in its expanded configuration. Thus, an enlarged gall bladder, for example, may be withdrawn through said expanded base member 14 and through bore 13a.

After the gall bladder or other organ or tissue has been removed, leading end 13 of plunger 12 is retracted from base member 14 and bias members 18 restore base member 14 to its repose configuration. The puncture opening closes naturally when the tool is withdrawn.

In the embodiment of FIGS. 1 and 2, each bias member 18 is held against longitudinal displacement by a pair of annular retention members collectively denoted 17. Annular grooves could also be formed in base member 14 and the bias members could be seated within said grooves; if the grooves are made sufficiently deep, the bias members may lie therewithin and be flush or even recessed with respect to the cylindrical surface of base member 14.

The embodiment of FIG. 6 eliminates retention members 17 and avoids use of grooves formed in the surface of base member 14. A plurality of cooperatively-positioned, transversely disposed, circumferentially-extending bores are formed in base members 14a, 14b, 14c and 14d and bias members 18 extend through said bores. This positioning of bias means 18 prevents any trauma that might be caused by retention members 17 without weakening base member 14 by forming grooves therein.

As mentioned earlier, FIG. 4 depicts trocar tool 10 in end view when bias members 18 are in repose; this is the configuration of base members 14 when the initial puncture is made with a trocar. FIG. 3 depicts base members 14a, 14b, 14c and 14d when they have been spread radially apart by insertion of leading end 13 of plunger 12 into the trailing end of said base member 14.

FIG. 5 provides a view like that of FIG. 3, but depicts an embodiment having eight base member parts; they are denoted 14a–h. In the embodiment of FIGS. 1–4 and in the embodiment of FIG. 5, the radially innermost end of each base member is flat and the longitudinal edges thereof are beveled as depicted. Such beveling ensures that the parts collectively mate with one another and form a closed or solid cylinder when bias members 18 are in repose, i.e., when leading end 13 of plunger 12 is not inserted into base member 14.

As depicted in FIG. 2, a flexible and resilient elastomeric seal 16a enwraps housing 16. Seal 16a has a central opening 16b formed therein that seals tightly around leading end 13 of plunger 12 when said leading end is disposed within base member 14.

A similar seal 11a having central opening 11b enwraps plunger handle 11. Seal 11a tightly seals around any surgical tool that is inserted through bore 13a of leading end 13 of plunger 12.

Housing 16 is advantageously structured to facilitate assembly of novel trocar tool 10. Note in FIG. 2 that it is formed of two parts, said parts being denoted 16b and 16c; ledge 16d is formed in part 16b to provide a seat for part 16c. This enables insertion of base member 14 into its operative position, i.e., part 16c is seated onto seat 16d after the trailing end 15(a–d) of base member 14 has been inserted into housing 16.

Flared trailing end 15(a–d) guides leading end 13 of plunger 12 into base member 14.

Moreover, a radially-extending annular flange 21 is also formed near trailing end 15(a–d) of said base member 14. The flange is positioned so that it abuts an inside surface of part 16b and flared trailing end 15(a–d) is sized so that it abuts an inside surface of part 16c as depicted. When base member 14 is expanded by insertion thereinto of leading end 13 of plunger 12, and contracted by removal of said leading end and the compression provided by bias members 18, said flared trailing end 15(a–d) and annular flange 21 slide along said respective surfaces 16b and 16c. In this way, housing 16 provides a guide means for base member 14 as it expands and contracts.

Figure 7:
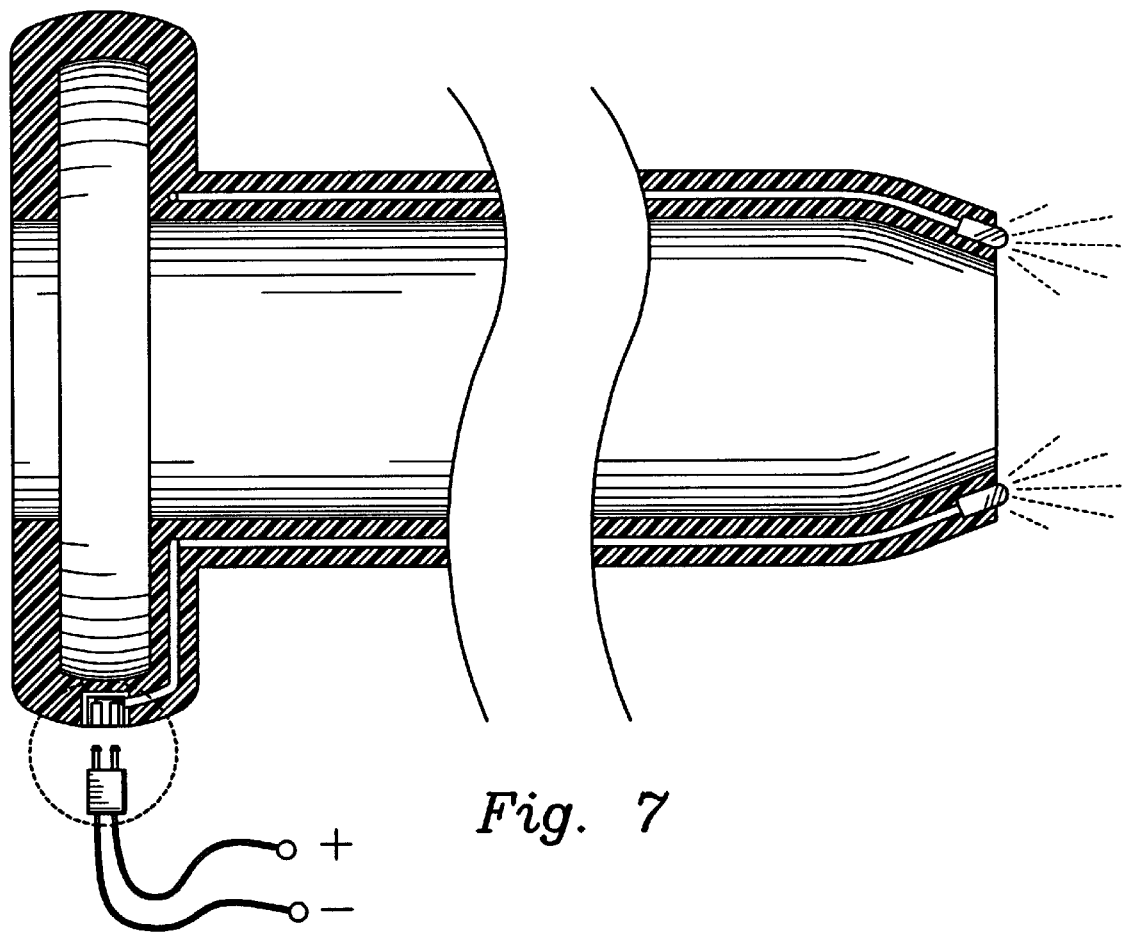
FIG. 7 is a broken, longitudinal sectional view of a second embodiment of the novel plunger.
Figure 8:
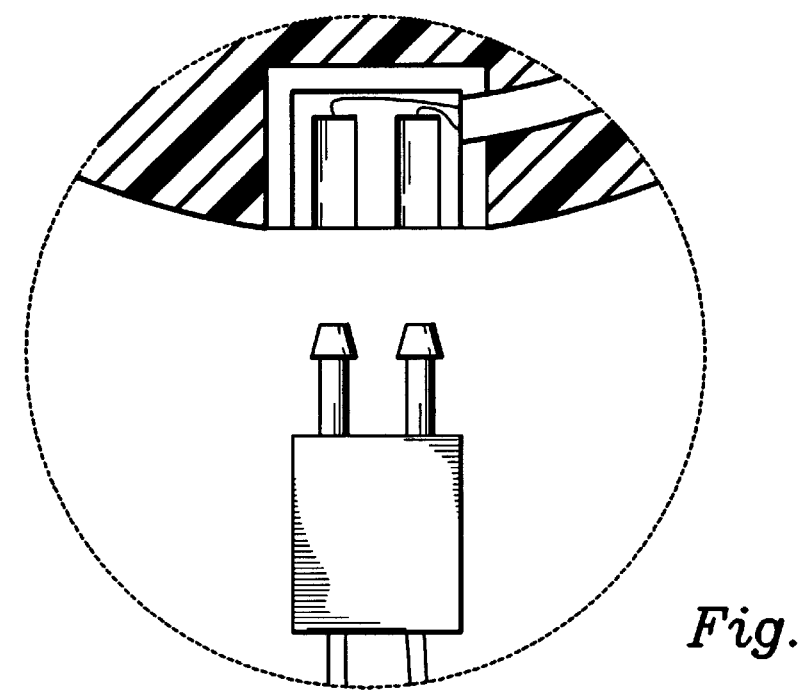
FIG. 8 is an enlarged view of the encircled area indicated in FIG. 7.

FIGS. 7 and 8 depict an alternative embodiment of plunger 12. Enlarged handle 11 of plunger 12 has an electrical socket 20 formed therein for releasably receiving electrical plug 22. The enlarged view of FIG. 8 reveals that electrical conductors, collectively denoted 24, extend from socket 20 to light bulbs, collectively denoted 26, that are positioned at the leading end of plunger 12. Suitable bores are formed in the cylindrical sidewalls of said plunger to accommodate said electrical leads. This enables illumination of the body cavity within which the leading end of plunger 12a is positioned. An alternative embodiment eliminates electrical conductors 24 in favor of optical fibers. In that alternative embodiment, plug 22 is connected to a remote source of light and not to an electrical power source.

A patient treated with the novel trocar tool of this invention will have a more comfortable recovery and a shorter recovery time after surgery than a patient treated with a conventional trocar tool because it enables retraction of even enlarged gall bladders and the like in the absence of a conventional incision.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A surgical tool, comprising:
    a base member having an elongate, cylindrical configuration;
    said base member having a leading end adapted for insertion through a puncture opening formed in a body cavity and a trailing end that remains external to said puncture opening;
    a housing for receiving said trailing end of said base member;
    said base member being formed of a plurality of separate parts, said parts being formed by cutting a cylindrical member with a plurality of longitudinally-extending, circumferentially-spaced apart cuts;
    a plurality of stretchable bias members disposed about said base member at predetermined, longitudinally-spaced intervals, to hold together the separate parts of said base member, said base member having a solid cylindrical configuration when said bias members are in repose;
    a hollow plunger having a leading end of cylindrical configuration;
    said leading end of said hollow plunger having a predetermined external diameter greater than a predetermined internal diameter of said base member when said bias members are in repose so that sliding insertion of said leading end of said hollow plunger into said trailing end of said base member causes the separate parts of said base member to expand radially outwardly with respect to a longitudinal axis of symmetry of said base member; and
    said leading end of said hollow plunger having a predetermined internal diameter that is greater than the internal diameter of said base member when said bias members are in repose;
    whereby insertion of said leading end of said hollow plunger into said base member enlarges said puncture opening.

2. The surgical tool of claim 1, wherein said housing for receiving said trailing end of said base member is transversely disposed with respect to a longitudinal axis of said base member and wherein said housing is sized so that it accommodates the trailing end of said base member when said base member is in an unexpanded configuration and when said base member is in a fully expanded configuration.

3. The surgical tool of claim 2, wherein said housing is hollow and centrally apertured at a trailing end thereof to accommodate entry of said leading end of said plunger into said base member.

4. The surgical tool of claim 3, further comprising a flexible and resilient seal means secured to said housing, said seal means being apertured to form a central aperture and said central aperture of said seal means being positioned in registration with said central aperture formed in said trailing end of said housing, said seal means sealing around said leading end of said plunger when said leading end of said plunger is disposed within said base member.

5. The surgical tool of claim 3, wherein said trailing end of said base member is flared radially outwardly at a predetermined angle to serve as a guide means for said leading end of said plunger and wherein said housing accommodates the flared trailing end.

6. The surgical tool of claim 5, further comprising an annular flange that extends radially outwardly from said base member and which is positioned in closely spaced relation to said flared trailing end and wherein said housing accommodates said annular flange.

7. The surgical tool of claim 6, wherein said housing includes a transversely disposed trailing wall and a transversely disposed leading wall, wherein a trailing edge of said flared trailing end of said base member abuts said trailing wall of said housing and wherein said annular flange abuts said leading wall of said housing, said housing providing a guide means for the base member as it expands and contracts upon insertion thereinto and withdrawal therefrom, respectively, of said leading end of said plunger.

8. The surgical tool of claim 1, wherein said hollow plunger further includes a handle means disposed at a trailing end of said plunger, said handle means being transversely disposed relative to a longitudinal axis of said leading end of said plunger.

9. The surgical tool of claim 8, wherein said handle means is hollow and centrally apertured at a trailing end thereof so that it is adapted to accommodate entry of a surgical tool.

10. The surgical tool of claim 9, further comprising a flexible and resilient seal means secured to said handle means, said seal means being apertured to form a central aperture and said central aperture of said seal means being positioned in registration with said central aperture formed in said handle means, said seal means sealing around said surgical tool when said surgical tool is disposed within said plunger.

* * * * *